(12) United States Patent
Kleinbloesem et al.

(10) Patent No.: US 9,139,815 B2
(45) Date of Patent: Sep. 22, 2015

(54) STEM CELLS DERIVED FROM BONE MARROW FOR TISSUE REGENERATION

(75) Inventors: Cornelis H. Kleinbloesem, Brummen (NL); Paul Giles, Liskeard (GB)

(73) Assignee: Pharma Pass II LLC, Irvine, CA (US)

( * ) Notice: Subject to any disclaimer, the term of this patent is extended or adjusted under 35 U.S.C. 154(b) by 1534 days.

(21) Appl. No.: 11/742,944

(22) Filed: May 1, 2007

(65) Prior Publication Data
US 2007/0265558 A1 Nov. 15, 2007

(51) Int. Cl.
| | | |
|---|---|---|
| *A01N 1/02* | (2006.01) | |
| *B01D 33/15* | (2006.01) | |
| *C12N 5/0775* | (2010.01) | |
| *A61M 1/02* | (2006.01) | |
| *A61M 1/36* | (2006.01) | |
| *A61K 35/12* | (2015.01) | |

(52) U.S. Cl.
CPC ............. *C12N 5/0663* (2013.01); *A61M 1/029* (2013.01); *A61K 2035/124* (2013.01); *A61M 1/3693* (2013.01)

(58) Field of Classification Search
CPC ................ A61K 2800/48; A61K 2800/5424; A61K 2800/5426; A61K 2800/594; A61K 8/042; A61K 8/731; A61K 8/737; A61K 8/8147; A61K 8/8158; A61K 8/817; A61K 8/86; A61K 2035/124
See application file for complete search history.

(56) References Cited

U.S. PATENT DOCUMENTS

| | | | | |
|---|---|---|---|---|
| 5,635,387 | A | * | 6/1997 | Fei et al. ........................ 435/378 |
| 5,840,502 | A | * | 11/1998 | Van Vlasselaer ............ 435/7.21 |
| 6,605,275 | B1 | * | 8/2003 | Boyse et al. .................. 424/93.7 |
| 2005/0130301 | A1 | * | 6/2005 | McKay et al. ................ 435/372 |

FOREIGN PATENT DOCUMENTS

| | | |
|---|---|---|
| WO | 01/20999 A1 | 3/2001 |
| WO | WO2004104553 A2 | 12/2004 |
| WO | 2005/004886 A1 | 1/2005 |

OTHER PUBLICATIONS

Boheler (J Physiol, 554.3: p. 592, The Physiological Society, 2003).*
Blazsek et al. Ontogenic emergence of the hematon, a morphogenetic stromal unit that supports multipotential hematopoietic progenitors in mouse bone marrow. BLOOD. 2000. vol. 96, No. 12. 3764-3771.
European Search Report for Patent Application No. EP06252326 issued by European Patent Office.
Deeg et al (Editor) Bone Marrow and Stem cell processing: A manual of current techniques. Oxford University press 1992.

* cited by examiner

*Primary Examiner* — Deborah Crouch
*Assistant Examiner* — Magdalene Sgagias
(74) *Attorney, Agent, or Firm* — Marsh Fischmann & Breyfogle LLP (57) ABSTRACT

The invention relates to stems cells derived from bone marrow, and uses thereof in tissue regeneration.

11 Claims, 3 Drawing Sheets

STEM CELLS DERIVED FROM BONE MARROW FOR TISSUE REGENERATION

FIELD OF THE INVENTION

The invention relates to cells and notably stem cells derived from bone marrow that can be used as a therapeutic preparation for cellular repair and improving tissue regeneration.

BACKGROUND OF THE INVENTION

Normal skin healing following a wound or injury is a complex and dynamic process involving the restoration of cellular structures and tissue layers following injury to the skin and other soft tissues. The healing process is generally thought to occur in three phases.

Firstly there is a clotting phase in which blood-thickening proteins and blood platelets seal a wound to prevent blood loss. Then there is an inflammatory phase in which white blood cells are sent to fight infection. Finally there is a repair phase in which tissue cells restore integrity to damaged areas.

All wound healing usually results in scarring to some extent which is caused by the incomplete restoration of initial skin structure and the disruption of the normal alignment of collagen fibers.

In addition, there are specific illnesses and diseases which can result in chronic skin wound and injuries, such as diabetes ulcers and ulcerous wounds. Also other conditions, such as paralysis and old age, can result in serious skin injuries as a result of pressure inflicted wounds such as eschars.

The muscular cardiac tissue is made of cardiomyocytes. These specialized forms of muscle cells are not capable of regeneration following injury in the adult. Common injuries to the heart muscle occur in ischemic heart attacks during which blood flow to the heart is restricted and the cardiac muscle is damaged through hypoxia. Patients suffering from heart infarct require both the restoration of blood supply to the heart and the regeneration of the damaged heart muscle.

The central nervous system composed of neurons and other nerve cells is generally incapable of regeneration in the adult and the peripheral nervous system is only capable of limited regeneration. Illnesses that commonly result in central nervous system damage are multiple sclerosis and amyotrophic lateral sclerosis. Incidents that commonly result in central nervous system damage are spinal cord damage and cerebral vascular accidents.

Urinary incontinence can result from damage to the sphincters of the urethra.

Various conditions can result in liver damage including viral hepatitis, cirrhosis, steatohepatitis and liver cancer.

Similarly damage and degeneration of the pancreas can result in diabetes.

Arthritis is a form of degradation and damage to the joints between bones.

There is thus a need to produce therapeutic strategies for improving these conditions, whether they are the result of a pathology or the natural imperfection of skin-healing, or incapacity for heart tissue or nervous tissue or cartilage or joints or liver or urethral sphincters to regenerate or diabetes caused by the degeneration of pancreas. Additionally there is a need for therapeutic strategies for promoting angiogenesis generally and specifically for treating erectile dysfunction.

Fathke et al (Stem Cells 2004; 22:812-822) have shown that following an injection of bone marrow stem cells in mice, these stem cells contributed to the population of regenerated skin cells in normal conditions. It was further shown that bone marrow stem cells contributed to dermal fibroblasts regeneration and transcribed Collagen type I and III, Collagen type III being specific to these stem cells derived from bone marrow. The stem cells were transplanted either systemically by injection into the bloodstream of a different animal to the donor or directly in the bone marrow of the recipient. No improvement on the quality or speed of the healing was shown.

In the publication by Bang O. Y et al, Ann Neurology 2005, June; 57(6): 874-82, there is described the transplantation of autologous mesenchymal stem cells being bone marrow mononuclear cells for the treatment of ischemic strokes. These cells were separated by the Ficoll density separation of bone marrow and were cultured and expanded before re-implantation. In addition they did not express CD34 or CD45. No functional improvement was observed following treatment.

In the publication by Mazzini et al, (The Lancet 2004; 354: 1936-1937), there is described the transplantation in the spinal cord of autologous mesenchymal stem cells for the treatment of amyotrophic lateral sclerosis. The results described only showed a slowing down of the decline of the forced vital capacity of some patients but no improvement.

SUMMARY OF THE INVENTION

The Applicant has discovered a novel method of extraction and separation of bone marrow cells that enables the increase of their therapeutic potency. The cells extracted by this method are capable of regenerating in vivo skin, blood vessels, nervous system and heart muscle.

Some of the various aspects of the invention concern:

1. A process for separating bone marrow cells comprising the steps of:
   a) centrifuging the bone marrow;
   b) collecting the buffy coat layer formed after step a);
   c) centrifuging the buffy coat obtained at step b); and
   d) collecting the buffy coat layer formed after step c).

2. The process for separating bone marrow cells according to item 1 wherein steps a) and c) are carried out at 1500 G.

3. The process for separating bone marrow cells according to item 1 or 2 wherein steps a) and c) are carried out at 18° C.

4. The process for separating bone marrow cells according to any of the preceding items wherein step a) is carried out for at least about 20 minutes and step c) is carried out for at least about 10 minutes, preferably for up to 20 minutes and more preferably for at least about 20 minutes.

5. The process for separating bone marrow cells according to any of the preceding items wherein at step b) red blood cells beneath the buffy coat layer are collected with the buffy coat layer, and the volume of the red blood cells collected is between 1 to 20 times, preferably 1 to 10 times, more preferably 2 to 5 times and even more preferably 5 times, that of the buffy coat layer.

6. The process for separating bone marrow cells according to any of the preceding items comprising additional steps between step b) and c) comprising the steps of:
   b1) collecting a volume of red blood cells beneath the volume collected at step b), wherein the volume of red blood cells collected is between 1 to 20 times, preferably 1 to 10 times, more preferably 2 to 5 times and even more preferably 5 times, that of the buffy coat;
   c1) centrifuging the volume of red blood cells collected at step b1);
   d1) collecting the buffy coat layer formed after step c1); and
   e1) mixing the buffy coat collected after step d1) with the buffy coat collected after step c).

7. The buffy coat obtainable by the process according to any of the preceding items.

8. The buffy coat according to item 7 wherein cells contained in the buffy coat express CD 45 or CD 34.

9. The bone marrow derived cells of the buffy coat according to any of items 7 or 8.

10. The cells according to item 9, wherein the cells are stem cells.

11. The cells according to items 9 or 10 wherein the cells express CD 45 or CD 34.

12. The cells according to any of items 9 to 11 wherein the cells are of the haematopoietic or mesenchymal lineage.

13. The cells according to items 9 to 12 for their use in therapy.

14. The cells according to item 13 for their use in tissue regeneration.

15. The cells according to item 13 or 14 for their use in the therapeutical treatment of a central nervous system disease or injury.

16. The cells for the use according to the item 15 wherein the disease or injury is selected from the group consisting of spinal cord injury, multiple sclerosis, cerebral vascular accident and amyotrophic lateral sclerosis 17. The cells according to item 13 or 14 for their use in healing a skin wound.

18. The cells for their use according to the item 17 wherein the skin wound is selected from the group consisting of skin wounds resulting from diabetes, ulcers, surgery, cosmetic surgery and burns.

19. The cells according to item 13 or 14 for their use in promoting angiogenesis.

20. The cells according to item 13 or 14 for their use in treating erectile dysfunction.

21. The cells according to item 13 or 14 for their use in treating type 1 or type 2 diabetes.

22. The cells according to item 13 or 14 for their use in treating arthritis.

23. The cells according to item 13 or 14 for their use in treating liver damage.

24. The cells according to item 13 or 14 for their use in treating urinary incontinence.

25. The cells according to any one of items 13 to 24 which are autologous.

Both the foregoing summary of some of the various aspects of the invention and the following detailed description of particular embodiments are exemplary for the purpose of enabling one of ordinary skill in the art to make and use the invention. Other aspects, features, applications and adaptations will be readily apparent to those skilled in the art from the foregoing summary, the following detailed description of some embodiments, the figures and the claims.

DETAILED DESCRIPTION OF EMBODIMENTS OF THE INVENTION

The applicant has shown that it is possible to use bone marrow derived cells and notably stem cells to treat damaged tissues by promoting and increasing healing in human and in other mammals. The applicant has developed a novel method of extraction and separation which enables the concentration of bone marrow cell extracts, the increase in potency of these cells and the concentration and selection of specific therapeutic bone marrow cells. These cells can be used to improve the healing of incisions and wounds following surgery in general and in cosmetic surgery.

By a wound, it is meant, any break, tear, loss of continuity or incision of the skin, whether or not complications occur.

The cells extracted from bone marrow and suitable for the invention can be stem cells and are also referred to as mesenchymal stem cells. For the purpose of this description stem cells is intended not to be narrowly restricted to cells capable both of division in an undifferentiated state and to differentiation, but generally to cells capable of regenerating a tissue whether by differentiation or by promoting the division and regeneration of other cells or activating other cells.

The stem cells can be derived from any source but can also be autologous and thus derived from the individual on which treatment will be performed, so as to prevent rejection from the host.

Stem cells derived from bone marrow can be obtained by extracting bone marrow from suitable long or flat bones. Flat bones are preferred as they contain more bone marrow. An especially suitable bone is the hipbone.

Bone marrow is first extracted surgically. Various methods are commonly known in surgery to effect the extraction of bone marrow. The stem cells are then separated and concentrated in accordance with example 1. Important features of the process are the separation steps using two centrifugation cycles with a low spin speed. The steps used include:

1) the separation by centrifugation of the Buffy coat from the plasma and red blood cell layers.
2) The pipetting of the buffy coat layers with approximately 0.5 ml of the red blood cell layer immediately beneath.
3) the further separation by centrifugation of the Buffy coat from the plasma and red blood cell layers.
4) The pipetting of the final buffy coat layer.

Additionally and optionally after step 2) it is possible to pipette into separate tubes the top 0.5 ml of the red blood cell layer which is left over after the buffy coat removal. This new sample can be centrifuged as for the buffy coat extract in step 3 and processed for buffy coat extraction as in step 4. The additional buffy coat extract resulting form the top 0.5 ml of red blood cell layer can be added to the final buffy coat extract and is an additional source of bone marrow derived stem cells.

The spin profile which involves a low G and a progressive increase to the maximum valued ensures maximum separation of the bone marrow into its constituent parts, concentrating the stem cells in the Buffy Coat and minimising any residual cells in the other two layers. The spin profile also produces a Buffy Coat that can subsequently be manipulated.

The technique used in the Buffy Coat manipulation ensures that the boundary layers between this and the adjacent layers are also captured to ensure maximum retention of cells. Subsequently, the impact of the inclusion of the interface material is reduced by the next stage of the process.

The use of second spin cycle, with a modified profile, allows further concentration of the stem cells without physical damage to the cells and allows control of both the end volume and final concentrations of stem cells. This control is allows the returned samples to be tailored to the requirements of the transplant.

The result of using a second spin produces an improved result, additional separation of the layers and, consequently, a concentration of the cells in the Buffy Coat, but no significant reduction in viability of the cells.

Bone marrow stem cells suitable for the invention have been shown to be nucleated cells expressing CD 45 or CD 34 or alternatively to be present in a mixture with nucleated cells expressing CD 45 or CD 34. Other markers that can be used for control or for sorting are leukocyte markers. The stem cells suitable for the invention are not limited to, but include those from the haematopoietic or mesenchymal stem cell pool of the bone marrow.

This description is not to be understood as limiting the invention only to the stems cells bearing the markers described. Any stem cell capable of differentiating into a cell type participating in, or promoting, tissue regeneration is equally suitable for the purpose of the present invention.

A suitable amount of cells to be delivered in a suitable physiologically compatible medium is 20 to 200 million cells of which 2 to 20 million are expressing CD34, in 2 to 10 ml of cell suspension. The unused excess solution of cells can be frozen in order to be re-used for subsequent treatment.

EXAMPLES

The following section provides examples of the instant invention as well as best modes, which should not be considered as limiting the scope of the instant invention.

Example 1

Buffy Coat Extraction

In this example is described the technique for separating and concentrating the bone marrow derived cells that are used for transplantation and tissue regeneration in accordance with the invention. The process must be carried out aseptically in a clean room environment with suitable bio confinement equipment well known in the art.

| Definitions: | |
| --- | --- |
| BM | Bone Marrow |
| BC | Buffy Coat |
| CPA | Cryoprotective agent |
| DMSO | Dimethyl Sulphoxide |
| LFH | Laminar Flow Hood |
| LN | Liquid nitrogen |
| RBC | Red Blood Cell |

1. Transfer of BM from Collection Device to Centrifuge Tubes
a) Take one bone marrow collection tube, check the lid is on tight and thoroughly mix the contents.
b) Remove the small cap on the collection tubular connector and set aside on the sterile sheet.
c) Invert the collection tube directly above one of the sterile centrifugation tubes and gently push the plunger, or insert and push the temporary plunger, in to displace the contents into the centrifuge tube. Excessive force is not required must not be used.
d) Replace the smaller cap and set the empty collection tube aside.
e) Repeat the procedure for all collection tubes.
f) Fill the centrifugation tubes to a maximum level of 14 ml. Re-cap as filled before proceeding to the next available tube.

2. Centrifugation 1st Spin
a) Load the centrifuge tubes into the bucket liner.
b) Load into the centrifuge and run the centrifuge. The centrifugation is performed at 18° C. for 20 minutes at an RCF (rotational centrifugal force) of 1500 g. The acceleration to the maximum g and the deceleration from the maximum g are performed in about 60 seconds.

Figure 1:
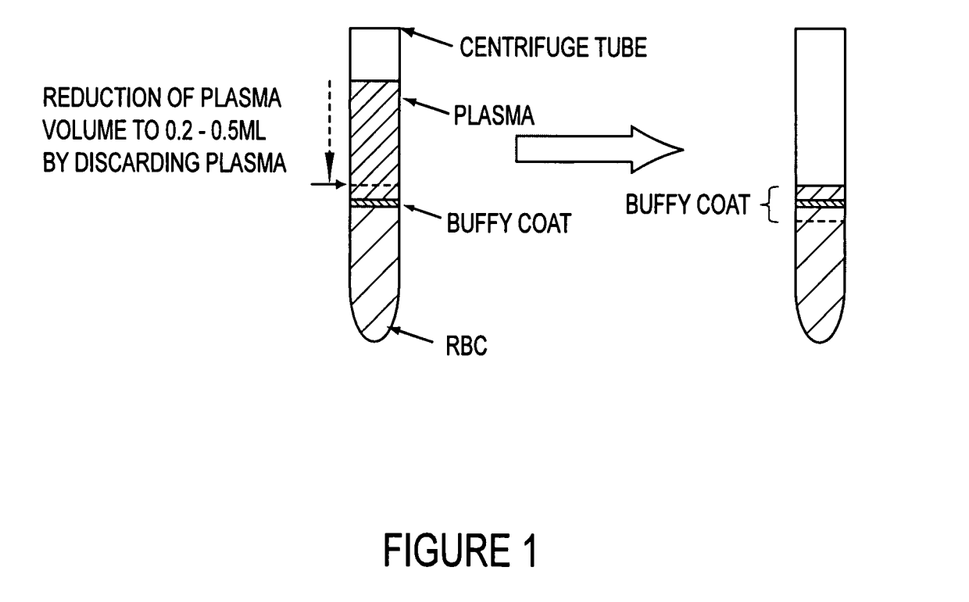
FIG. 1 shows the bone marrow after the first centrifuge cycle, the resulting buffy coat layer and the removal of the supernatant plasma.
Figure 2:
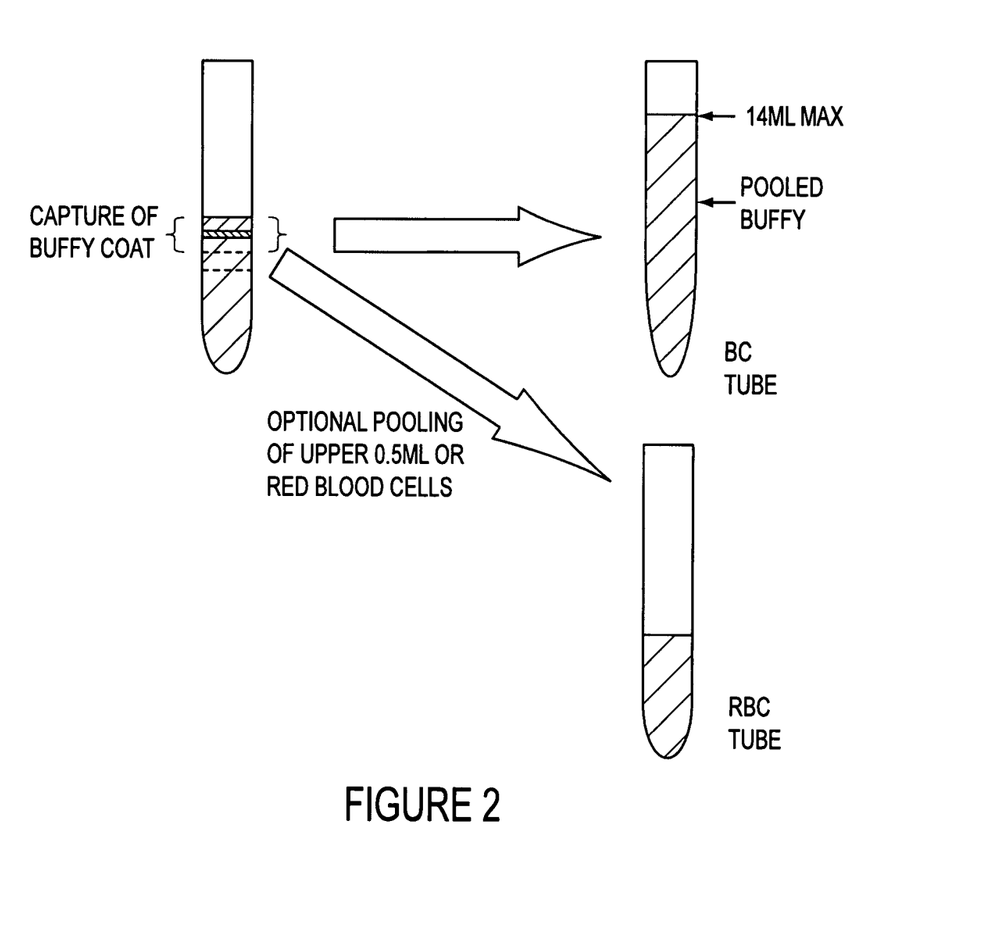
FIG. 2 shows the buffy coat layer after the removal of the supernatant plasma following the first centrifuge cycle. It additionally shows the pooling of the buffy coat layer into the BC tube and the optional pooling of the top 0.5 ml of the red blood cell layer into the RBC tube.

3. Capture the Buffy Coat—1st Collection
a) At the end of the first spin remove the tubes.
b) Remove the lid of one centrifuge tube containing separated bone marrow (the "BM-centrifuge" tube) and place inside down on a sterile sheet.
c) Remove a pipette from its sterile wrapping, and with the bulb under positive pressure insert into the neck of the opened BM-centrifuge tube. Carefully withdraw plasma, without disturbing the buffy coat (repeat until approximately 0.2-0.5 ml of plasma remains above the buffy coat (FIG. 1). When removing the bulk of the plasma, discard into beaker. Repeat this procedure for all BM-centrifuge tubes until all the excess plasma has been removed.
d) Return to each BM-centrifuge tube in turn and capture the buffy coat. Pool the buffy coat into fresh, empty sterile centrifuge tubes (the "BC-centrifuge" tube), as follows. Remove a pipette from the sterile wrapping and with its bulb under positive pressure insert into the neck of the opened BM-centrifuge tube. Pass the tip of the pipette through the small plasma layer and draw up the buffy coat. Rotate the tip around the surface of the buffy coat and capture the thick and viscous layer and up to 0.5 ml of red cells from directly beneath the layer (FIG. 2). Decant into a BC-centrifuge tube.
e) Optionally Pool the top 0.5 ml of red blood cells that remain after the buffy coat was pipetted, from the BM-centrifuge tubes into the "RBC-centrifuge" tubes (red blood cell)) (FIG. 2), recap and stand in rack.

4. Centrifugation 2nd Spin
a) Load the centrifuge tubes (BC & pooled-RBC) into the bucket liner.
b) Load into the centrifuge and run centrifuge. The centrifugation is performed at 18° C. for 10 to 20 minutes at an RCF (rotational centrifugal force) of 1500 g. The acceleration to the maximum g and the deceleration from the maximum g are performed in about 60 seconds. The centrifugation time is chosen according to the condition of the Bone Marrow at the end of the first spin cycle; if a highly concentrated end product is required, the spin length is increased towards the maximum time. This produces a strongly defined concentrated buffy coat layer. A visual check may be carried out after 10 minutes of spinning to assess the state of the buffy coat layer.

Figure 3:
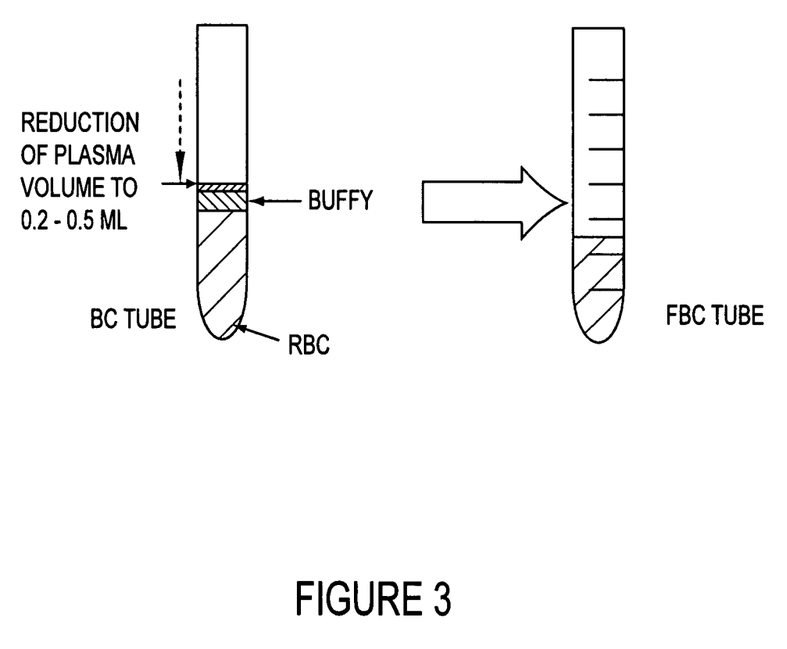
FIG. 3 shows the final buffy coat layer after the second centrifuge cycle and the removal of the plasma supernatant. The final buffy coat extract is pooled into the FBC tube.

5. Capture the Buffy Coat—2nd Collection
a) At the end of the second spin remove the tubes.
b) Remove the lid of the BC-centrifuge tubes containing separated bone marrow and place face down on the sterile sheet.
c) Remove a pipette from its sterile wrapper and under positive pressure insert into the neck of the opened BC-centrifuge tube. Carefully withdraw plasma, without disturbing the buffy coat. Repeat until approximately 0.2-0.5 ml of plasma remains above the buffy coat (FIG. 3). Repeat this procedure for all BC-centrifuge tubes until all the required plasma has been removed.

d) Return to each BC-centrifuge tube in turn and capture the buffy coat. Pool the buffy coats into a fresh, clean centrifuge tube (the "FBC-centrifuge" tube (final buffy coat)) as follows. Remove a pipette from its sterile wrapper and under positive pressure insert into the neck of the opened BC-centrifuge tube. Pass the tip of the pipette through the small plasma layer and draw up the buffy coat. Rotate the tip around the surface of the buffy coat and capture the thick and viscous layer and up to 0.5 ml of red cells from directly beneath the layer (FIG. 3). Decant into the fresh FBC-centrifuge tube.

e) Optionally The RBC tube once spun will have formed another buffy coat layer. It is possible to perform the same buffy coat capture for the RBC-centrifuge tube. This buffy coat can optionally be mixed with the buffy coat in the FBC-centrifuge tube.

Optional Freezing with DMSO

It is possible to freeze the cells obtained. An advantage is that the freezing stops their degradation and increases their survival and therapeutic potency. The steps required are as follows:

a) Ensure the Control Rate Freezer is at the start temperature before adding the DMSO.
b) Load the LFH with an ambot of DMSO.
c) Calculate the volume of DMSO-Dextran mix required to achieve a 10% v/v mix.
d) Place two chilled gel packs around the buffy Coat tube and hold upright.
e) Rapidly add the DMSO initiating a 10 minute countdown on the prepared digital clock. On replacing lid, agitate the tube to mix the DMSO & buffy coat. The addition of DMSO to the cells produces an exothermic reaction and the excess heat, will be dissipated by the chilled gel packs. Ensure the gel packs remain in contact with the specimen. Ensure that the cap remains tightly fixed.
f) After 2 minutes, dispense the buffy-DMSO mix equally into cryovials. Cap securely and set each tube on the lowest position of separate cryo-canes (to ensure each tube will be fully immersed in liquid nitrogen at the plunge stage of the cryo-run). Run the Control Rate Freezer to bring the temperature to −140° C.

Overall the advantages of this extraction and concentration technique are that:
1) The volume of transplanted cells is minimised while maximising the number of undamaged cells retained.
2) The volume of haematocrit and plasma which add nothing to the transplant process and which can be detrimental, is reduced
3) The amount of cryo-preservant used is reduced and consequently the potential hazardous effects to the patient is limited.
4) The concentration of the resultant cells can be controlled and total cells/volume ratio tailored to the requirements of the therapeutic treatment.

Example 2

Collection of Bone Marrow Cells

The following tools and apparatus were used: the collection spot was sterilized using a 1× sterile drape sheet with a hole of 75×90 cm, a sterile gauze pad 20×20 cm and a sterile solution to sterilize the collection spot such as Isobetadine. Local anesthesia was performed using a pull up needle 21G (green), a 1×5 ml. syringe and a subcutaneous-needle 23G (blue). The anesthetic was either 2% Scandicain® or 2% lidocain. The bone marrow aspiration was performed using a Sherwood Medical Sternum/Iliac aspiration needle 16G, Sarstedt Li-Heparin syringes with Luer connection and a small tray for transporting the syringes to the operating room.

The bone marrow was collected in a sanitized environment and the following steps were performed:

1. The collection spot was chosen to be either left or right spina iliaca posterior ("SIPS").
2. The patient was put in appropriate position (in bed horizontal or sitting position).
3. Skin disinfection was performed approximately 10 cm around the SIPS with Isobetadine polyvidone-iodium and the three gauze dappers for several times.
4. The sterile area was covered with a sterile drape sheet with a hole (75×90 cm).
5. The local anaesthetic was applied with approximately 5-10 ml Scandicain at 2% on the collection spot, approximately 1 cm around the SIPS using the 5 ml syringe 23G needle (blue).
6. The area around the SIPS was treated with the local anaesthetic needle.
7. Scandocaine is applied and there is required approximately 3-5 minutes of waiting for the taking up.
8. The bone marrow-aspiration needle was positioned in the Spongiosa of the SIPS.
9. The Mandrin was put away and laid it down on sterile area.
10. The sterile Li-Heparine 9 ml syringe was put up.
11. 9 ml bone marrow per tube was taken and gently mixed with the heparin and, the Mandarin needle was positioned approximately 0.5 cm deeper in the bone.
12. The collection was repeated several times with a new 9 ml tube.
13. A total volume of 5 tubes of bone marrow was taken from at least 5 to 10 different needle positions.
14. Use of a syringe lock ferrule, to effect a sterile closure.

Example 3

Central Nervous System Regeneration

A total of 10 Spinal Cord Injury (SCI), 7 Cerebral Vascular Accident (CVA), 4 Multiple Sclerosis (MS) and 2 Amyotrophic Lateral Sclerosis (ALS) patients were treated with their own bone marrow derived stem cells. Stem cells were separated under clean room conditions and frozen until administration in accordance with example 1.

The cells were applied to the spinal cord or brain directly. CVA, MS and ALS patients were treated with intrathecal and intravenous (i.v.) administration. Both in patients with SCI and CVA significant improvements in sensation and movement were noted in the vast majority of the patients. Development of these functional recoveries took several months.

Also in MS and ALS patients significant improvements were made. All patients were stabilized and for the observation period no deteriorations were observed. The most striking observation is that the spasm disappeared in all Stroke and MS cases and in most of the SCI patients.

The cell transplantations were safe and well tolerated. There were no complications except for one patient in which there was wound leaking for 3 weeks. After the intrathecal administration patients encountered malaise, back pain and vomiting for up to 5 days. Otherwise the treatments were well tolerated.

The treatments were carried out as follows.
Methods
SCI Patients

Stable patients (with injuries older than 9 months) were selected. The spinal cord did not have deep atrophy or show complete dissection on MRI. Both para and tetraplegic patients participated.

CVA Patients

Stable patients (injury older than 1 year old) were selected. The infarcted area should be accessible by neuronavigation, minimizing the possibility of damage to unaffected areas. Patients should have severe neurological symptoms (hemiparesis, spasm). In patients where no neuronavigation was possible because of deep infarction, intrathecal administration was done followed by i.v. infusion.

MS Patients

Patients with secondary progressive forms of MS were selected. Patients had clear lesion on the MRI in the brain and or spine.

ALS Patients

For ALS patients no specific exclusion criteria was used, except that in view of the treating physician the patient should be stable enough for the treatment.

Stem Cells

Stem cells were derived from autologous bone marrow. Up to 200 ml of bone marrow was collected. Processing was done under GMP conditions.

Stem cells were separated in accordance with the invention and the total volume was approximately reduced by 50 fold. The sample was frozen at a controlled rate to a final temperature below −180° C. in nitrogen vapour until transportation. As a cryoprotectant 10% DMSO-dextran was added. Immediately after transplantation sample was thawed and administered). At least 5 million stem cells were administered. The concentration of CD34 positive cells was in the range of 5-17 million.

Surgical Procedure for SCI

Under general anaesthesia laminectomy was done at the level of the injury. Dura was cut and under microscopic view stem cells where injected with a microsyringe into the lesion. This started at the top of the lesion followed by several injections into the lesion. In total 50 to 20 mini injections of 50 to 100 microliter where given. The total volume was maximally 1.5 ml of cell suspension. After completion the dura was closed and 2 to 3 days after surgery patients went home for further recovery and rehabilitation for at least 4 to 6 months.

Surgical Procedure for CVA

Under general anaesthesia incision was made in the skull. A hole was drilled and the dura cut. Under navigation with a Medtronic device, a catheter, with multiple holes about 1 cm apart, was guided to the infarcted area. The cell suspension (up to 8 ml) was injected into at least two different areas. After 1 to 3 days patients went home for further recovery and rehabilitation.

Intrathecal Administration and i.v. Administration in Patients with Stroke, MS and ALS.

First an intra venous—(i.v.) infusion of 250 ml saline was given over 10 minutes. A 16 g. needle was put at the lower lumbar level into the spinal canal. This was done under local anaesthesia. About 2 ml of fluid was taken in a syringe and mixed with 2 ml of cell suspension. This was injected slowly over 2 min. i.v. administration was done through a vein in the arm of the patient over 5 min.

Assessment of the Patients

Neurological assessments were done before and at 1, 2 and 6 months after surgery. From this a description was made individually.

SCI Patients

A summary of the demographic data of the patients is given in Table 1. A summary of the results contained after stem cell transplantation is given in Table 2. An individual description of each patient is given below.

Patient 1

Patient 1 was a 39 year old male. He suffered from a surgical complication after hernia surgery 9 months before. His injury was complete at the level of C5-C6. He had no sensation or movement below his breast. He was suffering from spasm in his left leg. He had no sensation or movement in his left fingers. In his right hand he could move two fingers slightly. His blood pressure was normal. He had Neurogenic bladder and no sphincter control.

After 1 month sensation in both arms and fingers came back. He could move three fingers on his left hand and all fingers on his right hand. He had movement of toes and cold/warm sensations in his legs. After 3 months all fingers could move and he was able to perform complicated tasks such as handwriting. Movement in leg (push and pull) using a walker he was able to walk about 20 steps. After strong exercise he increased weekly his performance. He clearly felt his abdomen and bladder. However there was no sphincter or bladder control yet. He also regained penile erections. At 6 months the improvement continued but at a very slow pace. A Sep-EMG was largely improved at 3 months after surgery. The MRI at 6 months suggested that the lesion was at least 30% smaller Patient 2

Patient 2 was a 36 year old male with a complete injury at C4-C5. He had no sensation below his breasts. Also no feelings in his hands and fingers. His accident was a diving accident 2 years back. He suffered from spasm in both legs. He had Neurogenic bladder with very frequently urinary tract infections and no sphincter control. 1 Month after surgery patient had feelings of burning and electricity in both his arms and legs. At 3 months he could move his left hand and fingers and toes of his left leg. After 4 months he could walk a few steps with a walker. Feeling in bladder and abdomen came back after 2 months. Also warm and cold feelings came back. A Sep-EMG after 6 months appear to be almost normal. The MRI showed a decrease in the area of the lesion of about 50%.

Patient 3

Patient 3 was a 21 year old male. He suffered 2 years before from a car accident and was injured at the level of T7. His injury was complete. On the CT scan almost a complete dissection was suggested. Nevertheless he suffered from severe spasm in his left leg. Even after 6 months no improvement in his clinical conditions was observed and on CT scan no difference was observed.

Patient 4

Patient 4 was a 42 year old male. He suffered 2 years before from a motorcycle accident and was injured at the level of C4-C5. He has no sensation or movement from his breast. Sometimes he had some sensations in the muscles of his legs. He suffers from severe spasm in both legs. There was no sensation in his left hand and some sensation in his right middle finger. Left and right arm movement was possible. He had neurogenic bladder and no sphincter control. He had a blood pressure 100/70 mm Hg or lower leading to dizziness. After one month he got back sensation in his left arm, fingers left and right. Sensation level moved down to waist. Also cold/warm sensations in his leg and sensation in his toes. He also had feelings in his abdomen. Blood pressure is normal (130/80 mm Hg). Spasms occurred but were not painful anymore. At 2 months he felt a burning sensation (electric like) through his arms and legs and muscle pain in arms, breast, back and legs. Also finger muscles were painful. At 4 months there was a feeling down to his toes. His muscles in his back as well as abdomen recovered completely, enabling him to move his body up and down when sitting in his wheelchair. Also feeling in his abdomen and sphincter was recovered. The feeling of electricity was intensified.

Patient 5

Patient 5 was a 55 year old female. She suffered from a spinal infarction due to blood clot at the level of T4-T5. It was an incomplete injury with limited sensation. Also there was no cold/warm sensation. Due to severe spasm in both legs she got a baclofen pump. She could stand on her spasm for a few seconds. She suffered form neurogenic bladder and no sphincter control. After surgery she experienced some wound healing problems, but after 4 weeks this healed. At one month after the surgery she had sensation in bowel and some cold/warm sensation. Strength of her muscles in her legs improved, but no change in spasm was observed. Now 4 months after the operation she had feeling in her bladder and forces were still increasing.

Patient 6

Patient 6 was a 36 year old male. He suffered from a complete injury at the level of C4-C5 due to an accident at work as a construction worker. He had no sensation from his breast, little spasm, no finger functions, neurogenic bladder and no sphincter function. The patient regained little sensation in his arm and legs. No movements was observed. Improvement is very slow.

Patient 7

Patient 7 was a 22 year old male. He suffered from a complete injury at the level of T6 due to a car accident. It was a complete lesion resulting in no sensation, no movement and also no spasm. The patient had neurogenic bladder and no sphincter control. There were no apparent improvements after 3 months.

Patient 8

Patient 8 is a 21 year old male. He suffered a complete lesion at T7 due to a car accident 8 years back. He had no sensation or movement. He suffered from neurogenic bladder and no sphincter control. After 4 weeks he regained bladder feeling and a burning sensation described as electricity in his legs. He also regained autonomic nervous system functions including no more cold feeling in his legs. After 2 months the sensations increased and control of bladder was sometimes achieved.

Patient 9

Patient 9 is a 40 year old male who suffered a complete lesion at C4-C5 due to a car accident. The patient has some spasm, no hand control and no finger movement or sensation. He suffered from neurogenic bladder and absence of sphincter control. Patient suffered from severe decubitus. After four weeks he felt burning sensations. Sensation came back in his arms and fingers. Spasms were reduced and no longer painful. After 3 months he was able to move his fingers in both arms. Burning sensation was increasing all the time.

Patient 10

Patient 10 was a 32 year old male with incomplete injury at C5-C6 with some sensation and movement in hand and fingers and some cold/warm sensations. There was abduction left and right. He suffered from spasms and from neurogenic bladder and no sphincter control. He had no need for ventilation support. After 4 weeks sweating and burning sensation on his legs came back. His fingers could move much easier. He also suffered fewer spasms. The patient also regained bowel sensations.

Demographic Data of SCI Patients Before Surgery.

The table 1a and 1b shown below summarise the result of the patients' clinical assessment pre-treatment.

TABLE 1a

| Nr | Age | Lesion | Complete | Bladder feeling | Bowel feeling | Spasm | Ventilation support |
|----|-----|--------|----------|-----------------|---------------|-------|---------------------|
| 1  | 39  | C5-C6  | y        | n               | n             | y     | N                   |
| 2  | 36  | C4-C5  | y        | n               | n             | y     | N                   |
| 3  | 21  | T7     | y        | n               | n             | y     | N                   |
| 4  | 42  | C4-C5  | y        | n               | n             | y     | N                   |
| 5  | 55  | T4-T5  | n        | n               | n             | y     | N                   |
| 6  | 36  | C4-C5  | y        | n               | n             | y/n   | N                   |
| 7  | 22  | T6-T7  | y        | n               | n             | n     | N                   |
| 8  | 21  | T7-T8  | y        | n               | n             | y     | N                   |
| 9  | 40  | C4-C5  | y        | n               | n             | y     | N                   |
| 10 | 32  | C5-C6  | y        | n               | n             | y     | N                   | y means yes,
n means no.

TABLE 1b

Results SCI patients after surgery.

| | Feeling | | | | | movement | | | | | |
| | leg | | arm | | Fingers | | Leg | | arm | | fingers | |
| Nr | L | R | L | R | Lh | Rh | L | R | L | R | Lh | Rh |
| 1  | n | n | y | n | n  | Y  | n | n | y | y | n  | y  |
| 2  | n | n | y | n | n  | N  | y | n | y | n | n  | n  |
| 3  | n | n | y | y | y  | Y  | n | n | y | y | y  | y  |
| 4  | n | n | y | y | y  | N  | n | n | y | n | y  | n  |
| 5  | n | n | y | y | y  | Y  | n | n | y | y | y  | y  |
| 6  | n | n | y | y | n  | N  | n | n | y | y | n  | n  |
| 7  | n | n | y | y | y  | Y  | n | n | y | y | y  | y  |
| 8  | n | n | y | y | y  | Y  | n | n | y | y | y  | y  |
| 9  | n | n | y | n | n  | N  | n | n | y | n | n  | n  |
| 10 | n | n | y | n | y  | N  | n | n | y | y | y  | n  | y means yes,
n means no.

Tables 2a and 2b shown below summarise the result of the patients' clinical assessment post-treatment.

TABLE 2a

| Nr | Time after surgery | Lesion | Bladder feeling | Bowel feeling | Spasm | Ventilation support |
|----|--------------------|--------|-----------------|---------------|-------|---------------------|
| 1  | 9 months | C5-C6 | Y | Y | N   | N |
| 2  | 9 months | C4-C5 | Y | Y | N   | N |
| 3  | 9 months | T7    | N | N | Y   | N |
| 4  | 5 months | C4-C5 | Y | Y | Y/N | N |
| 5  | 5 months | T4-T5 | Y | Y | Y   | N |
| 6  | 3 months | C4-C5 | N | N | N   | N |
| 7  | 3 months | T6-T7 | N | N | Y   | N |
| 8  | 2 months | T7-T8 | Y | N | Y   | N |
| 9  | 2 months | C4-C5 | N | N | N   | N |
| 10 | 2 months | C5-C6 | N | N | N   | N |

Y means yes,
N means no.

TABLE 2b

| | Feeling | | | | | movement | | | | | |
| | Leg | | Arm | | Fingers | | leg | | arm | | fingers | |
| Nr | L | R | L | R | Lh | Rh | L | R | L | R | Lh | Rh |
| 1  | Y | Y | Y | Y | Y | Y | Y | Y | Y | Y | Y | Y |
| 2  | Y | Y | Y | Y | Y | Y | Y | Y | Y | Y | Y | Y |

TABLE 2b-continued

| | Feeling | | | | | | movement | | | | | |
|---|---|---|---|---|---|---|---|---|---|---|---|---|
| | Leg | | Arm | | Fingers | | leg | | arm | | fingers | |
| Nr | L | R | L | R | Lh | Rh | L | R | L | R | Lh | Rh |
| 3 | N | N | | | | | N | N | | | | |
| 4 | Y | Y | Y | Y | Y | Y | N | N | Y | Y | N | N |
| 5 | Y | Y | Y | Y | Y | Y | Y/N | Y/N | Y | Y | Y | Y |
| 6 | Y | Y | Y | Y | Y | Y | N | N | N | N | N | N |
| 7 | N | N | Y | Y | Y | Y | N | N | Y | Y | Y | Y |
| 8 | Y | Y | Y | Y | Y | Y | N | N | Y | Y | Y | Y |
| 9 | Y | Y | Y | Y | Y | Y | N | N | N | N | Y | Y |
| 10 | Y | Y | N | N | Y | Y | N | N | N | N | N | N |

Y means yes,
N means no.

CVA Patients

A Summary of the demographic data of the patients is given in Table 3. A summary of the results obtained after stem cell transplantation is given in Table 4. An individual description of each patient is given below.

Patient 1

Patient 1 was a 54 year old male. He suffered from a stroke 4 years ago due to valvular insufficiency. He had a media infarction right sided or resulting in hemi paresis with aphasia and cognitive disturbances. He also had "tunnel vision" disturbances of taste and no warm/cold sensation. His coordination was disturbed. Spasm on his left leg and arm/hand was severe. He was mentally depressed. He had a high blood pressure and was sweating at the paralyzed site, indicating a disturbed autonomic nervous system. Sensation on his left side came back one month after the surgery, as well as trunk control. His taste completely recovered. The cold feeling of his arm disappeared. Spasm disappeared almost completely in his leg. His walking ability improved dramatically after 3 months. There was no need for wheelchair under normal conditions. Also his speech and his mood improved. He also had no more defecation problems. The patient could open his affected hand. Patient did regularly physical therapy and is now still improving. Nine months after the surgery his fine motoric movements are still improving. He can use his left hand to take objects. Also walking as well as speech further improved. Spasm is completely gone. A newly made MRI scan showed that the infarction was 20-25% reduced in size.

Patient 2

Patient 2 was a 69 year old male who suffered from a stroke 5 years before. He had a very large infarction at the right side front parietal. This resulted is hemi paresis with aphasia. He had double tongue feeling and loss of taste. He also had spasms on his feet and leg. Blood pressure was normal. Memory was affected as well.

One month after surgery he got back warm/cold sensation and his legs were "prickling" and feeling of electricity. Also his taste partially came back. Smoking was a pleasurable sensation again. After 3 months his spasm in his feet disappeared, he could move his toes again. Also some strength is his leg came back. However 4 months after surgery he had a severe car accident leading to a hip replacement. After this accident most of the improvements disappeared.

Patient 3

Patient 3 was a 34 year old male. He suffered from 2 car accidents respectively 2 and 6 years before. He had a large frontal parietal infarction at the left side, but also right temporal, consistent with a trauma capitis resulting in contusio cerebri. This resulted in tetra paresis, severe spasm on his right side of both arm and leg, aphasia and lack of memory. Also sensation was lacking on his right side. 3 weeks after the surgery he had less spasm in arm and leg. He also has a better coordination. His speech improved already dramatically. After 3 months he could walk more easily and straighter. He was also more alert than before.

Patient 4

Patient 4 is a 42 year old male. He suffered from a stroke one year ago. He had a media infarction on his left side due to hypertension and smoking. This resulted in a hemi paresis on his right side, with aphasia and lack of memory. He was sweating abundantly in his right side, suggesting also an effect on the autonomous nervous system. Also he had no feeling in his mouth and no taste anymore. He was suffering from spasm on his right side (arm and leg). After the surgery he got back feeling in his mouth and right side of his breast. Sweating disappeared completely and walking was also improved. His spasm disappeared almost completely. He could move his leg and arm and open his hand where the spasm was located. Speech was easier. His leg had a normal temperature and sweating was also normalised. After 3 months his general well being and quality of life had been greatly improved.

Patient 5

Patient 5 was a 61 year old male. He suffered from a stroke due to atrium fibrillation. This resulted in a total hemi paresis of the left side, with no sensibility, facial paresis, speech problems, neglect and aphasia. There was also a visual extinction phenomena left sided. Patient was also suffering from spasm on hand, arm and legs. Three weeks after the surgery, patient was less sensitive to daylight. Speech marginally improved. Otherwise no changes yet. After 3 months the signs did not improve with the exception of alertness.

Patient 6

Patient 6 was a 62 year old female. She suffered from an infarction at the brain stem on the left side 6 years ago while dancing. This resulted in a hemi paresis in the right side. Both her leg and arm were spastic. Her speech was severely impaired. Her left eye was affected as well, resulting in almost complete blindness. During the first 8 weeks after the infusion nothing changed. Then slowly spasm disappeared, light reflex in her left eye returned and 2 weeks later also vision for more than 80%. She reported spontaneously that she was able to read. Feeling in her right side was partly restored. Also coordination improved slightly. Her speech also improved and was more fluent. Improvement was still continuing.

Patient 7

Patient 7 was a 42 year old female. She is suffering from severe brain damage due to lack of oxygen during birth. She is wheelchair bound and could not speak normally. She was also mentally handicapped with severe spasticity and disturbed facial tone. After 1 month spasticity was severely diminished in legs and arms. She was sitting more upright in wheelchair. An important improvement in level of alertness was observed. Facial paralysis diminished and there was no more involuntary loss of saliva. Her muscle force in arm improved and during physical exercise she could lift up a 1 kg object with her right arm.

Demographic Data for CVA Patients Before Surgery.

The table 3a and 3b shown below summarise the result of the patients' clinical assessment pre-treatment.

TABLE 3a

| Nr | Age | Lesion | Taste | Vision | Speech | Memory | Remarks |
|---|---|---|---|---|---|---|---|
| 1 | 54 | rh | − | − | − | − | |
| 2 | 69 | rh | − | + | − | − | |

TABLE 3a-continued

| Nr | Age | Lesion | Taste | Vision | Speech | Memory | Remarks |
|---|---|---|---|---|---|---|---|
| 3 | 34 | lh/rh | + | + | – | +/– | tetra paresis. |
| 4 | 42 | lh | – | + | – | – | |
| 5 | 61 | lh | + | + | – | – | light sensitive. |
| 6 | 62 | lh | + | – | – | – | |
| 7 | 42 | lh | – | + | – | – | | lh means left hemisphere,
rh means right hemisphere.
– means affected,
+ means not affected.

TABLE 3b

| | Spasm | | | Feeling | | | Movement | | | | |
|---|---|---|---|---|---|---|---|---|---|---|---|
| | leg | | arm | | Leg | | arm | | leg | | arm |
| Nr | L | R | L | R | L | R | L | R | L | R | L | R |
| 1 | – | + | – | + | – | + | – | + | – | + | – | + |
| 2 | – | + | – | + | – | + | – | + | – | + | – | + |
| 3 | – | – | – | – | – | – | – | – | – | – | – | – |
| 4 | + | – | + | – | + | – | + | – | + | – | + | – |
| 5 | + | – | + | – | + | – | + | – | + | – | + | – |
| 6 | + | – | + | – | + | – | + | – | + | – | + | – |
| 7 | – | – | – | – | – | – | – | – | – | – | – | – |

– means affected,
+ means not affected.

Results for CVA Patients After Surgery.

The table 4a and 4b shown below summarise the result of the patients' clinical assessment post-treatment.

TABLE 4a

| Nr | Time after surgery | Taste | Vision | Speech | Memory | Remarks |
|---|---|---|---|---|---|---|
| 1 | 8 months | + | + | + | + | vision: tunnel vision as well as defecation improved. |
| 2 | 8 months | + | – | + | – | Had major car accident 14 weeks after surgery with hip replacement. |
| 3 | 3 months | – | – | + | + | |
| 4 | 3 months | – | – | + | – | feeling in his mouth, no more sweating on paralyzed side. |
| 5 | 3 months | – | + | + | – | less light sensitive. |
| 6 | 6 months | – | + | + | + | |
| 7 | 7 months | – | – | + | + | Facial paresis less | lh means left hemisphere,
rh means right hemisphere.
+ means improved,
– means no change.

TABLE 4b

| | Spasm | | | Feeling | | | Movement | | | | |
|---|---|---|---|---|---|---|---|---|---|---|---|
| | leg | | arm | | Leg | | arm | | leg | | Arm |
| Nr | L | R | L | R | L | R | L | R | L | R | L | R |
| 1 | + | – | + | – | + | – | + | – | + | – | + | – |
| 2 | + | – | – | – | + | – | + | – | + | – | – | – |
| 3 | + | – | + | – | – | – | – | – | + | + | – | – |
| 4 | + | (+) | – | – | – | + | – | + | – | + | – | – |
| 5 | + | – | – | – | – | – | – | – | – | – | – | – |
| 6 | – | + | – | + | – | + | – | + | – | – | – | – |
| 7 | + | + | + | + | + | + | + | + | – | – | + | + |

+ means improved,
– means no change.

ALS Patients

An individual description of each patient is given below.

Patient 1

Patient 1 was a 72 year old female with ALS for 3 years. She could not speak and was completely disabled. She could only lie in bed. Movement of legs and arms was possible but difficult. Use of fingers was limited. Her lung capacity was not measurable. Immediate after the stem cell treatment her general condition improved. Speaking is easier and her condition has stabilized 2 months after therapy.

Patient 2

Patient 2 was a 52 year old male diagnosed with ALS 3 months ago. His only symptoms were speech problems. After 2 months his condition had not deteriorated. His speech improved slightly.

MS Patients

An individual description of each patient is given below.

Patient 1

Patient 1 was a 42 year old male diagnosed with MS for 12 years. For 3 years he was secondary progressive. He could not move his legs and had also no feeling in his legs. Further he was very tired. He had defecation problems and was suffering from continuous spasm in his legs. He is bound to a wheelchair.

He received i.v. injection of stem cells as intrathecal administration was not possible (dry-puncture). On the same evening his spasm disappeared. He was very tired for 3 days, but recovered quickly. After 2 weeks feeling in his toe and legs came back slowly. After 2 months he was able to move his toes and lower legs. His force came back and now he can exercise about 4-5 watt over 15 minutes. His previous exercise level was nil. His defecation was almost normal and he recovered morning erections. Mental function has improved.

The patient was clear minded and can formulate well. His reflexes in his leg were similar to those in his arms and there were no more hyper reflexes. His vision had also improved. No anti spasm medication was necessary.

Patient 2

Patient 2 was a 41 year old female with secondary progressive MS since 15 years. She was completely disabled and could not speak or swallow. Vision was disturbed. There was no feeling or movement in legs. She was suffering from spasm and was incontinent. Patient received i.v. injection of stem cells. The number of bone marrow cells was reduced to $1.5 \times 16^6$ cells. After 3 weeks the spasms disappeared in her legs and arms. Speech improved slowly. Defecation improved. After 3 months no further improvements were noted and a second infusion was planned.

Patient 3

Patient 3 was a 62 year old female suffering from MS for more than 15 years. For 3 years she had been secondary progressive. She was suffering from severe pain and spasms in her legs and total body. Swallowing and eating was very difficult. She had many ulcers of about 1 mm² on her legs. She was permanently in a wheelchair. Her skin on her face was itching all the time. Within 3 days after the cell therapy spasticity diminished and after 2 weeks it was completely gone. Her ulcer on her legs completely closed within 3-5 days. After 2 weeks she was able to stand unaided for 30 seconds, which was impossible before. Eating and swallowing of food was completely normal. Her vision improved (no more double vision) and speech as well. MS pain had almost completely disappeared and mentally she was fine. Typical MS tiredness disappeared. Anti spasm medication was reduced to almost nothing.

Patient 4

Patient 4 was a 39 year old male with a history of MS for the last 12 years and the last 3 years in secondary progressive form. He could walk unaided for up to 100 meters. He was suffering from spasm in his arms. He was very tired and had defecation problems. His vision was also disturbed. Up to one week after the intrathecal administration the patient was very tired and suffered pain in his lower back and legs. Spasm in his arms completely disappeared after 1 week. His general well being had improved and he was restarting exercise.

Discussion and Conclusion

Bone marrow derived stem cell obtained with the extraction techniques in accordance with example 1 were applied for therapy in 16 patients, 11 with Spinal Cord Injury (SCI) and 5 with Cerebral Vascular Accident (CVA). Surgery was without complications, except for 1 SCI patient, where there was wound leakage for 3 weeks. Stem cell treatment was well tolerated and no adverse reactions to therapy were noted in any patients.

There was a large inter individual variability in the number of cells collected. There was at least a 5 fold range. Since the volume of injection is very small in SCI patients (about 1.5 ml) cells were as concentrated as possible. The exact number of cells to be applied could not be calculated precisely. Only in one patient was there no effect observed. In all other patients at least some improvement or strong improvement was observed. The duration of recovery is also an important factor. The longest treated patient had the most effect. The recovery seems therefore slowly progressing over months. The duration for the effects to be observed was variable. The stem cell therapy applied in patients with SCI, CVA, MS and ALS seems safe and was well tolerated.

Example 4

Treatment of Diabetes and Restoration of Erectile Function

In this test 6 patients diagnosed with Diabetes Mellitus type 2 and suffering form erectile problems were treated with autologous adult stem cells taken from the hip bone. Table 5a shows a description of the patients.

TABLE 5a description of patients' condition.

| | Pat. 1 | Pat. 2 | Pat. 3 | Pat. 4 | Pat. 5 | Pat. 6 | average |
|---|---|---|---|---|---|---|---|
| Duration of complaints (years) | 7 | 6 | 1 | 1 | 0.3 | 1 | 2.7 |
| Previous treatment | Sildenafil Elastic bands Injections | Sildenafil | Life style adjustments | Sildenafil | Sildenafil | | |
| Other diseases | Diabetes type 2 | Diabetes type 2 Dislipidemy Obesitas Cardiovascular disease | Diabetes type 2 Arterial Hypertension | Diabetes type 2 Arterial Hypertension Previous treatment of Fimosis No sensation in Glans penis | Diabetes type 2 Arterial Hypertension Psoriasis Depression | Diabetes type 2 | |
| Level of impairment | Full | Full | Full | Full | Partial | full | |
| Age | 48 | 64 | 49 | 51 | 52 | 53 | 52.8 |

The bone marrow sample of about 150 ml was retrieved under local anesthetics. The bone marrow was collected through a needle which was inserted in the crista iliaca (ileac crest).

The Stem Cells were isolated and prepared for re-implantation as described in examples 1 and 2.

The Stem Cells were re-implanted by injecting them into the corpora cavernosa. The patients were treated with prophylactic Antibiotics.

The effect of the treatment was evaluated by both a subjective anamnesis on different subsequent dates as well as by a pre- and post-evaluation of the blood flow in the arteries of the corpera cavernosum (dorsal arteries)

Results

All 6 patients reported an increase in the quality, duration and tumescence. Only one patient did not report an effect on being able to have an ejaculation. This patient suffered from the after effects of a previous Fimosis operation, which left him without sensation in the glans penis.

On average the patients experienced a change in their ability to maintain an erection after 16 days. This data coincided with the duration until the patients were able to have an ejaculation.

Table 5b show the results of this study.

TABLE 5b changes to the duration of erection following treatment
Change in duration of erection

|        | Pat. 1 | Pat. 2 | Pat. 3 | Pat. 4 | Pat. 5 | Pat. 6 |
|--------|--------|--------|--------|--------|--------|--------|
| Day 0  |        |        |        |        |        |        |
| Day 8  |        | X      | X      |        |        | X      |
| Day 16 |        |        |        | X      |        |        |
| Day 24 | X      |        |        |        |        |        |
| Day 32 |        |        |        |        | X      |        |
| Day 40 |        |        |        |        |        |        |

The patients reported a gradual increase of the quality of their erections. The fact that all 6 patients reported to have an increased ability to maintain their erections longer was supported by the Doppler measurements of the blood supply to the corpus cavernous (shown at table 5c).

TABLE 5c changes to the blood supply to the corpus cavernous following treatment

| Patient | Before | After | % change |
|---------|--------|-------|----------|
| Systolic Speed Right Penis Artery (cm/sec) | | | |
| Pat. 1 | 15 | 19 | 26.6 |
| Pat. 2 | 11 | 26 | 136 |
| Pat. 3 | 23 | 30 | 30.4 |
| Pat. 4 | 30 | 37 | 23.3 |
| Pat. 5 | 15 | 20 | 33.3 |
| Pat. 6 | 30 | 32 | 6.66 |
| AVG | 20.7 | 27.3 | 42.7 |
| Systolic Speed Left Penis Artery (cm/sec) | | | |
| Pat. 1 | 30 | 46 | 53 |
| Pat. 2 | 11 | 28 | 154.54 |
| Pat. 3 | 23 | 40 | 74 |
| Pat. 4 | 30 | 37 | 23.3 |
| Pat. 5 | 10 | 29 | 190 |
| Pat. 6 | 30 | 32 | 6.66 |
| AVG | 22.3 | 35.3 | 83.6 |

There were no reports of adverse events during the evaluation period.

Example 5

Treatment of Arthritis

In this study 12 patients with osteo arthritis were treated with autologous stem cells taken from the hip bone (ileac crest). 9 Females and 3 males were treated and evaluated after 30, 60 and 90 days. The average age of the patients was 69.3 years (55-76). They suffered on average 5.4 years of osteo arthritis (0.2-10 years)

The patients were evaluated on the amount of pain experienced, the use of analgesics, the stability of the joints involved in the transplantation and of flexion and extension of the joints involved.

The bone marrow sample of about 150 ml was retrieved under local anesthetics. The bone marrow was collected through a needle which was inserted in the crista iliaca (ileac crest). The stem cells were isolated and prepared for re-implantation in accordance with example 1 and 2.

The Stem Cells were re-implanted by injecting 20 ml of stem cell preparation directly into the target joint. The patients were treated with prophylactic Antibiotics.

After the treatment 11 of 12 patients reported an improvement in the pain they experienced in the treated joints. The 12$^{th}$ patient reported this with the second return on day 60.

The patients experienced a significant benefit of the treatment (see table 6a, 6b and 6c).

TABLE 6a measure of pain before and after treatment.
Pain

|  | before | after |
|---|---|---|
| Pat. 1 | 9 | 0 |
| Pat. 2 | 9 | 3 |
| Pat. 3 | 8 | 4 |
| Pat. 4 | 7 | 4 |
| Pat. 5 | 8 | 4 |
| Pat. 6 | 9 | 2 |
| Pat. 7 | 9 | 3 |
| Pat. 8 | 9 | 3 |
| Pat. 9 | 9 | 2 |
| Pat. 10 | 9 | 3 |
| Pat. 11 | 8 | 3 |
| Pat. 12 | 8 | 4 |
| Average | 8.5 | 2.9 |
| Standard deviation | 0.67 | 1.16 |

This was supported by a significant change in the flexibility of the treated joints (table 6b).

TABLE 6b measure of joint flexibility before and after treatment.
Flexion/extension

|  | before | after |
|---|---|---|
| Pat. 1 | 2 | 8 |
| Pat. 2 | 2 | 6 |
| Pat. 3 | 4 | 6 |
| Pat. 4 | 3 | 7 |
| Pat. 5 | 2 | 6 |
| Pat. 6 | 2 | 6 |
| Pat. 7 | 2 | 6 |
| Pat. 8 | 2 | 6 |
| Pat. 9 | 4 | 7 |
| Pat. 10 | 4 | 9 |
| Pat. 11 | 2 | 7 |
| Pat. 12 | 4 | 6 |
| Average | 2.75 | 6.67 |
| Standard deviation | 0.97 | 0.98 |

The stability of the treated joints was increased after the treatment (table 6c).

TABLE 6c measure of joint stability before and after treatment.
Stability

|  | before | after |
|---|---|---|
| Pat. 1 | 4 | 7 |
| Pat. 2 | 4 | 7 |
| Pat. 3 | 4 | 6 |
| Pat. 4 | 3 | 6 |
| Pat. 5 | 4 | 7 |
| Pat. 6 | 3 | 8 |
| Pat. 7 | 4 | 6 |
| Pat. 8 | 6 | 9 |
| Pat. 9 | 5 | 9 |
| Pat. 10 | 2 | 7 |
| Pat. 11 | 5 | 7 |
| Pat. 12 | 4.0 | 7.2 |

TABLE 6c-continued measure of joint stability before and after treatment.

| | Stability | |
| --- | --- | --- |
| | before | after |
| Standard deviation | 1.10 | 1.08 |

5 patients reported adverse events. All 5 had pain in the area of the bone marrow retrieval site, 2 had pain in the treated joints and 1 experienced and hypersensitivity reaction to the bandage used and experienced an unexplained pain in knees and fingers.

Example 6

Treatment of Diabetes Mellitus Type 2

Five patients with diabetes mellitus type 2 were included. Their age ranged from 49-77 years.

Stem cells were extracted according to methods described in example I and II.

25 ml of bone marrow extract was infused by angiography through the spleenic artery and the hepatic artery.

Results:

The following results were obtained for each of the 5 patients.

Patient 1: reduction in insuline use by 60 percent after 3 months

Patient 2: no insuline use after 2 months

Patient 3: reduction in insuline use by 50 percent

Patient 4: reduction in oral antidiabetics by 80 percent after 2 months

Patient 5: reduction in insuline use by 60 percent after 2 months

Blood glucose was normal after the dose reductions.

The invention claimed is:

1. A method for separating bone marrow cells comprising the steps of:
   a) first centrifuging the bone marrow;
   b) first collecting a first buffy coat layer and also collecting a layer of red cells from directly beneath the first buffy coat formed after step a) wherein the volume of red blood cells beneath the first buffy coat layer collected is between 1 to 20 times that of the first buffy coat layer;
   c) second centrifuging the first buffy coat with the volume of red blood cells collected at step b); and
   d) second collecting a second buffy coat layer formed after step c).

2. The method according to claim 1, wherein steps a) and c) are carried out at 1500 G.

3. The method according to claim 1, wherein steps a) and c) are carried out at 18° C.

4. The method for separating bone marrow cells according to claim 1 wherein step a) is carried out for at least about 20 minutes and step c) is carried out for at least about 10 minutes, preferably for up to 20 minutes and more preferably for at least about 20 minutes.

5. The method for separating bone marrow cells according to claim 1 comprising additional steps between step b) and c) comprising the steps of:
   b1) collecting into at least one separate container a volume of remaining red blood cells left over the removal of the first buffy coat layer and volume of red blood cells collected at step b);
   c1) centrifuging the volume of red blood cells collected at step b1);
   d1) collecting a third buffy coat layer formed after step c1); and
   e1) mixing the third buffy coat collected after step d1) with the second buffy coat collected after step d).

6. The method for separating bone marrow cells according to claim 1, wherein: the first centrifuging comprises separating components of the bone marrow to form a first layered product comprising the first buffy coat layer formed between a first red blood cell layer and a first plasma layer; and the first collecting comprises removing the first buffy coat layer from the first layered product.

7. The method for separating bone marrow cells according to claim 6 wherein: the second centrifuging comprising forming a second layered product comprising the second buffy coat layer; and the second collecting comprises removing the second buffy coat layer from the second layered product.

8. The method for separating bone marrow cells according to claim 7, wherein the removing the first buffy coat layer from the first layered product comprises: selectively removing at least a portion of the first plasma layer from adjacent the first buffy coat layer in the first layered product; and thereafter selectively removing the first buffy coat layer from adjacent to at least a portion of a red blood cell layer.

9. The method for separating bone marrow cells according to claim 6, wherein steps a) and c) are carried out at 1500 G.

10. The method for separating bone marrow cells according to claim 6, wherein steps a) and c) are carried out at 18° C.

11. The method for separating bone marrow cells according to claim 1, wherein the second centrifuging is performed with the first buffy coat layer pooled in a container with other buffy coat layers collected during separately performing steps a) and b) on other bone marrow.

* * * * *

UNITED STATES PATENT AND TRADEMARK OFFICE
CERTIFICATE OF CORRECTION

| | | |
|---|---|---|
| PATENT NO. | : 9,139,815 B2 | Page 1 of 1 |
| APPLICATION NO. | : 11/742944 | |
| DATED | : September 22, 2015 | |
| INVENTOR(S) | : Cornelis H. Kleinbloesem and Paul Giles | |

It is certified that error appears in the above-identified patent and that said Letters Patent is hereby corrected as shown below:

Title Page, insert item --(30), Foreign Application Priority Data, May 2, 2006 (EP)....06252326.1--

In the Specification

Column 4, Line 54, delete "form" and insert --from--

Column 11, Line 13, delete "form" and insert --from--

Column 18, Line 15, delete "form" and insert --from--

Column 21, Line 25, delete "spleenic" and insert --splenic--

Column 21, Line 29, delete "insuline" and insert --insulin--

Column 21, Line 31, delete "insuline" and insert --insulin--

Column 21, Line 32, delete "insuline" and insert --insulin--

Column 21, Line 35, delete "insuline" and insert --insulin--

Signed and Sealed this
First Day of March, 2016

Michelle K. Lee
*Director of the United States Patent and Trademark Office*